(12) United States Patent
Gill et al.

(10) Patent No.: US 7,578,934 B2
(45) Date of Patent: Aug. 25, 2009

(54) CHROMATOGRAPHIC COLUMN SEAL

(75) Inventors: Melvyn Gill, Gloucester (GB); Neil Francis Frazer, Gloucesershire (GB); John Graham Dunkley, Gloucestershire (GB); Geoff Purdom, Acton, MA (US)

(73) Assignee: Millipore Corporation, Billerica, MA (US)

( * ) Notice: Subject to any disclaimer, the term of this patent is extended or adjusted under 35 U.S.C. 154(b) by 701 days.

(21) Appl. No.: 11/247,025

(22) Filed: Oct. 11, 2005

(65) Prior Publication Data

US 2006/0027502 A1 Feb. 9, 2006

Related U.S. Application Data

(62) Division of application No. 10/779,991, filed on Feb. 17, 2004, now Pat. No. 6,984,318.

(60) Provisional application No. 60/456,591, filed on Mar. 21, 2003.

(51) Int. Cl.
*B01D 15/08* (2006.01)
(52) U.S. Cl. ............... 210/198.2; 210/656; 210/456
(58) Field of Classification Search ........... 210/635, 210/656, 659, 198.2, 198.3, 456; 95/82, 95/85; 96/101, 107
See application file for complete search history.

(56) References Cited

U.S. PATENT DOCUMENTS

| | | | |
|---|---|---|---|
| 3,265,215 A | 8/1966 | Emneus et al. | |
| 4,597,866 A | 7/1986 | Couillard | |
| 4,636,315 A | 1/1987 | Allen, Jr. | |
| 4,797,209 A | 1/1989 | Jackson | |
| 4,891,133 A | 1/1990 | Colvin, Jr. | |
| 4,927,531 A | 5/1990 | Sakamoto et al. | |
| 5,141,635 A | 8/1992 | Chabrol et al. | |
| 5,324,426 A | 6/1994 | Joseph et al. | |
| 5,378,361 A | 1/1995 | Baeckstrum et al. | |
| 6,001,253 A | 12/1999 | Conroy et al. | |
| 6,132,605 A | 10/2000 | Leavesley et al. | |
| 6,139,732 A | 10/2000 | Pelletier | |
| 6,224,760 B1 | 5/2001 | Davies et al. | |
| 6,736,974 B1 | 5/2004 | Mann | |

FOREIGN PATENT DOCUMENTS

EP 476996 3/1992

*Primary Examiner*—Ernest G Therkorn

(57) ABSTRACT

A seal on a movable top or bottom plate for use in a chromatography column. The plate is formed of a flow distributor connected to one or more movement rods that control the movement of the top plate within a chromatography column. The plate is formed of two pieces, a flow distributor and a seal plate. The seal plate is mounted on top of the flow distributor and has a seal that is essentially co-terminal with the outer edge of the flow distributor. The seal plate is attached to the flow distributor by one or more pins or threaded bolts and forms a space between them. The one or more pins contain one or more compression means for biasing the seal plate against the flow distributor. An opening is formed in the seal plate for the selective introduction of a pressurized energy source such as compressed air, gas or hydraulic fluid into the space to overcome the compression means. One or more seals are arranged between the seal plate and distributor to maintain the pressurized energy source between the two of them. Optionally the space may contain a closed bladder or reservoir connected to the opening to contain the pressurized energy source.

14 Claims, 4 Drawing Sheets

CHROMATOGRAPHIC COLUMN SEAL

CROSS REFERENCE-RELATED APPLICATIONS

This application is a Divisional Application of U.S. patent application Ser. No. 10/779,991, filed on Feb. 17, 2004 now U.S. Pat. No. 6,984,318, which claims the benefit of U.S. Provisional Application No. 60/456,591, filed on Mar. 21, 2003. The entire contents of the reference application are incorporated herein by reference.

The present invention relates to a seal for a flow distributor in a chromatographic column. More particularly, it relates to a positively engaged seal that is released with pneumatic or hydraulic pressure.

BACKGROUND OF THE INVENTION

Chromatography columns are generally formed of three basic components, a column body, typically in the form of a hollow cylinder; a bottom plate which seals off the bottom of the column and which typically includes an outlet from the column bottom and a top plate. At least one plate is movable within the column. Typically it is the top plate that is designed to move within the interior of the column body and seal against the inner walls when in place. Between the bottom and top plates one places a media used to remove the desired components from a fluid stream. The top plate is moved to be against the top of the media and often is used to slightly compress the media to form a fixed bed. The outer edge of the top plate contains a seal that forms a liquid tight seal between the top plate and the inner wall of the body so that no fluid escapes. It also contains an inlet into the space between the top and bottom plates. Both plates also have a screen or frit that is closest to the media so as to separate the inlet and the outlet from the media itself and to act as a flow distributor to help ensure even flow of the fluid through the bed of media.

The seal on the movable plate has been one of two designs. The first is an inflatable seal that, once the plate is in the desired position, is inflated with compressed air to expand the seal and form a liquid tight arrangement between the inner wall and the plate. When it is desired to move the plate, the pneumatic or hydraulic supply is removed and the seal deflates so as to allow room between the inner wall and the seal. This clearance is enough to allow the plate to move unhindered see U.S. Pat. No. 6,139,732 for example.

Problems with such seals are many. If the air or hydraulic supply is cut off during use of the column, the seal deflates and the bed is disturbed with loss of fluid around the deflated seal. Not only is the batch ruined (with the loss of product), the column now must be taken apart and sanitized and repacked before it can be restarted.

Additionally, the seals being elastomeric and inflatable are by their nature semipermeable and tend to lose air to the bed over time. This introduces air into an otherwise closed environment and reduces the efficiency of the column by blocking certain areas of the bed from fluid flow and/or drying out the media (rendering it inactive). For hydraulic pressurized seals there is a concern that in the event of rupturing the hydraulic fluid may cause contamination.

Lastly, if the air or hydraulic pressure is not properly regulated, the seal can be overinflated and caused to tear or burst.

The other alternative is to position the seal above the flow distributor and have a second plate portion located above the seal. The flow distributor and second plate portion are capable of moving relative to each other by a series of threaded rods. In the unsealed position, they are at a position furthest from each other. Once the flow distributor is at the desired position, the two pieces are moved relative to each other to compress the seal between them, causing it to expand outward and form a liquid tight seal with the inner wall. Typically, this is arranged by moving the second plate piece toward the flow distributor see U.S. Pat. No. 6,132,605 and EP 3476996 A2 for example.

Seals of this type are slow to activate and deactivate. Moreover, they can be easily over-compressed causing damage to the seal and other column components. What is desired is a seal that can have infinite adjustability so that it is not over compressed and can be set such that it is possible to dynamically adjust the seal in a longitudinal direction (that is to move the top plate while retaining a degree of sealing.) (As maybe required for certain packing operations).

Additionally, as relative motion between the two components is the force for creating the seal it has been found that the flow distributor often is moved away from the bed creating a gap which disturbs the flow characteristics of the column.

A preferred embodiment would be to have a single point for actuation of the seal which is both more convenient and less prone to manual error than having multiple points of actuation equi-spaced about the circumference as is taught by the existing art. However when the diameter of the column is in excess of 20 cm, it becomes increasingly difficult to engineer a single point manual actuation of the seal.

What is needed is a sealing device that is easily activated and deactivated and which is an improvement over the existing seals. The present invention is just such a device.

SUMMARY OF THE INVENTION

The present invention relates to a seal on a movable plate for use in a chromatography column. The plate is formed of a flow distributor connected to one or more movement rods that control the movement of the plate within a chromatography column. The plate is formed of two pieces, a flow distributor and a seal plate. The seal plate is mounted on top of the flow distributor and has a seal that is essentially co-terminal with the outer edge of the flow distributor. The seal plate is attached to the flow distributor by one or more pins or threaded bolts. The one or more pins contain one or more compression means for biasing the seal plate against the flow distributor. An opening is formed in the seal plate for the selective introduction of a pressurized energy source such as compressed air, gas or hydraulic fluid. One or more seals are arranged between the seal plate and distributor to maintain the pressurized energy source between the two of them.

In use, the compression means positively and normally biases the seal plate toward the flow distributor causing the seal to be compressed between the seal plate, the distributor and the inner wall of the column creating a liquid tight seal. When it is desired to move the plate in the column, such as to pack or unpack the chromatography bed, a pressurized energy source is introduced through the opening and into the space between the distributor and seal plate causing the plate to move away from the distributor and thereby relieving the compression on the seal and allowing the top plate to move freely in the column.

In one embodiment of the present invention, the flow distributor outer edge is tapered as is the seal so that they interact with each other.

In another embodiment, the seal is affixed to the seal plate.

In a further embodiment, there is a flexible reservoir, such as a contained bladder seal, between the seal plate and the distributor. The reservoir is attached to the opening to selectively receive and discharge the pressurized energy source.

In an additional embodiment, the pressurized energy source is compressed air, a compressed gas, such as helium or nitrogen, or a hydraulic fluid such as water, oil or an oil-like composite used in hydraulic systems.

In another embodiment, the compression means is selected from springs, elastomeric materials placed under load or pressurized gas or hydraulic pistons.

IN THE DRAWINGS

DETAILED DESCRIPTION

Figure 1:
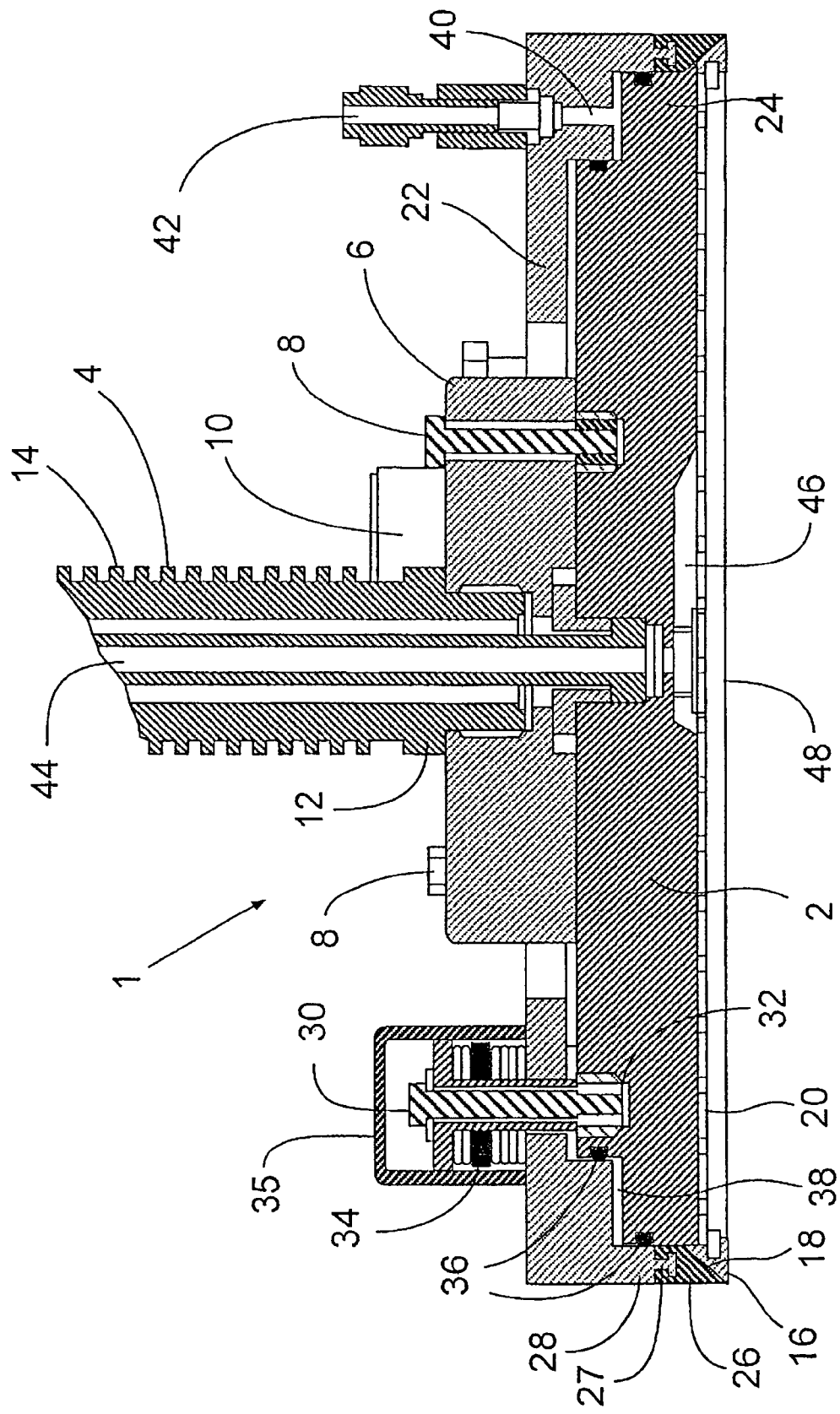
FIG. 1 shows a first embodiment of the present invention in cross-sectional view.

FIG. 1 shows a first embodiment of a movable plate 1 according to the present invention. In this embodiment the plate is described as being the top plate in a column. However, it equally is useful as the bottom plate when one wishes the bottom plate to be capable of movement or it may be used as both the top and bottom plate when one desires to make a column having two movable plates.

The flow distributor 2 is attached to one or more movement control rods 4, in this example, one central rod, by a retention plate 6. As shown, one or more bolts 8 extend through the retention plate 6 and into the top surface of the distributor 2. The rod 4 is also locked to the retention plate 6, in this instance by a shroud 10 that is part of the retention plate 6 and which traps an extended foot 12 of the rod 4. The rod 4 is shown as being threaded on its exterior surface. These threads 14 are mated to an opposite thread such as a nut that forms a portion of the column outside of and above the column (not shown). The rod 4 moves relative to this fixed nut of the device so that the top plate 1 may move in to and out of the column. Other means of attaching the movement rod to the plate 1 are well known and can be used in the present invention as well.

As shown, the outer edge 16 of the flow distributor 2 has an angled or tapered upper surface 18 of the distributor. The angle formed between the upper surface 18 and the bottom surface 20 may be from about 15° to about 80°, preferably between about 22.5° and about 75°, more preferably about 30° and 75°. While an angled edge is preferred as it provides additional force to the seal formed with the inner wall of the column (as will be explained below), it is not required.

A seal plate 22 is disposed around the outer periphery of the flow distributor 2. As shown in this embodiment, this plate 22 is in the form of an "L" with its longer surface adjacent the top surface of the flow distributor 2 and its shorter leg adjacent the side 24 of the flow distributor. Other designs are contemplated and can be used so long as they allow the seal of the present invention to be formed and used as contemplated by this invention.

The plate 22 has a seal 26 attached to its outer, lowermost portion 28. As shown, it is preferred that the seal 26 be positively attached to the plate so as to remain with plate 22 during movement. In this embodiment, it is held by a keyway 27 in the plate 22 that corresponds to a key in the seal 26. Other means to attach the seal 26 to the plate 22 may also be used including adhesives, a threaded attachment (preferably from the top of the seal 26 through the plate 22) and forming the seal 26 in place on the plate 22. In another embodiment the seal 26 need not be attached to the plate 22.

The plate 22 is attached to the flow distributor 2 by one or more pins 30. As shown, these pins 30 are bolts screwed into recesses 32 formed in the top surface of the flow distributor 2. Other devices such as a toggle handle on a smooth rod can also be used. The plate 22 is capable of movement along the pins 30 relative to the flow distributor 2. A compression means 34 on the pins 30 positively and normally biases the plate 22 against the flow distributor 2. In using a pin 30 such as a bolt, one can have infinite variability in adjusting the amount of pre-load force imparted by the compression means 34. It also allows one to have a safety feature such that in the event of loss of the pressurized energy (explained below) used to bias the plate 22 away from the flow distributor 2 one can still release the seal by unscrewing the bolts, thus relieving the normal bias of the seal 26. Also as shown in this embodiment, a cover 35 may be placed over the pins 30 and compression means 34 to keep them clean.

Also shown are one or more seals 36 between the plate 22 and flow distributor 2. A space 38 is formed between the plate 22 and flow distributor 2 in the area defined between the seals 36. This space 38 has an opening 40 that communicates to a source of pressurized energy 42. Pressurized energy 42 can be selectively supplied to and removed from the space 38 as desired. Also shown in the FIG. 1 is a flow tube 44 that extends through the rod 4 to an inlet 46 in the bottom surface 20 of the flow distributor 2. A screen or frit 48 extends across the bottom surface 20 of the flow distributor 2 allowing fluid from the inlet 46 to spread and then pass through the screen 48 into the chromatography column.

Figure 2:
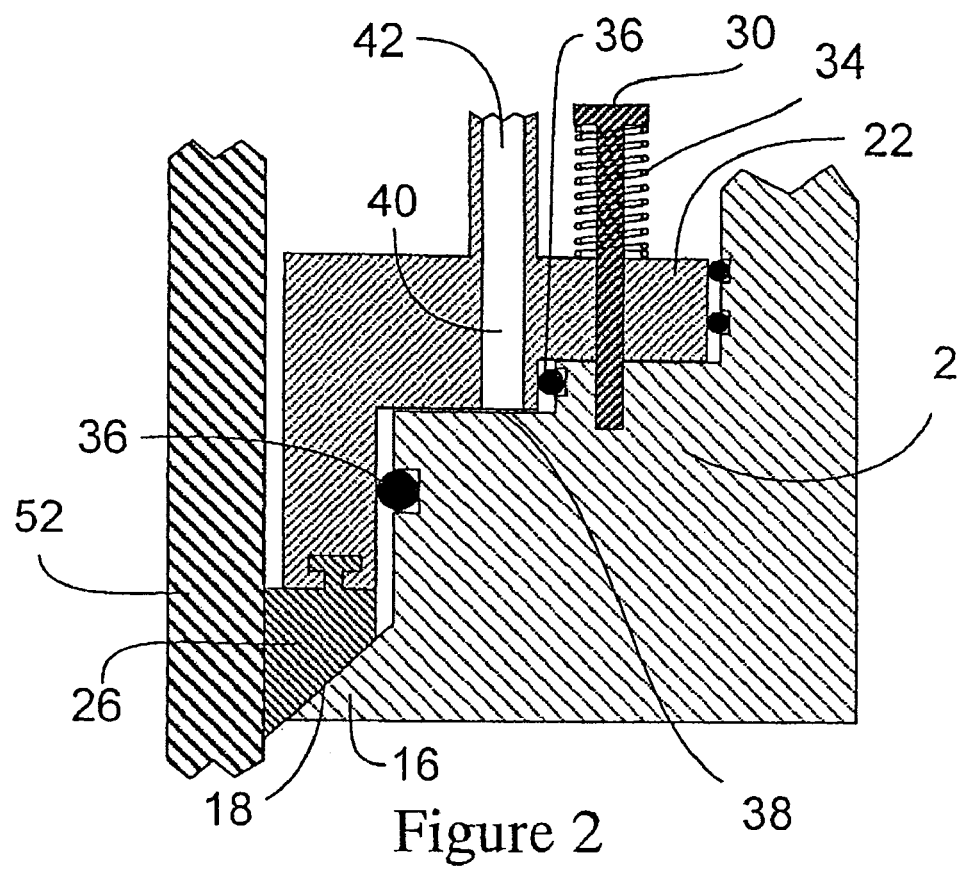
FIG. 2 shows a close up view of the first embodiment of the present invention of FIG. 1 in cross-sectional view.

FIG. 2 shows a partial cross-section of the flow distributor 2 inside a column body 52. As shown, the compression means 34 normally biases the plate 22 against the flow distributor 2. The seal 26 is compressed against the other angled edge 18 of the flow distributor 2 and the inner surface of the column body 52 forming a fluid tight seal.

Figure 3:
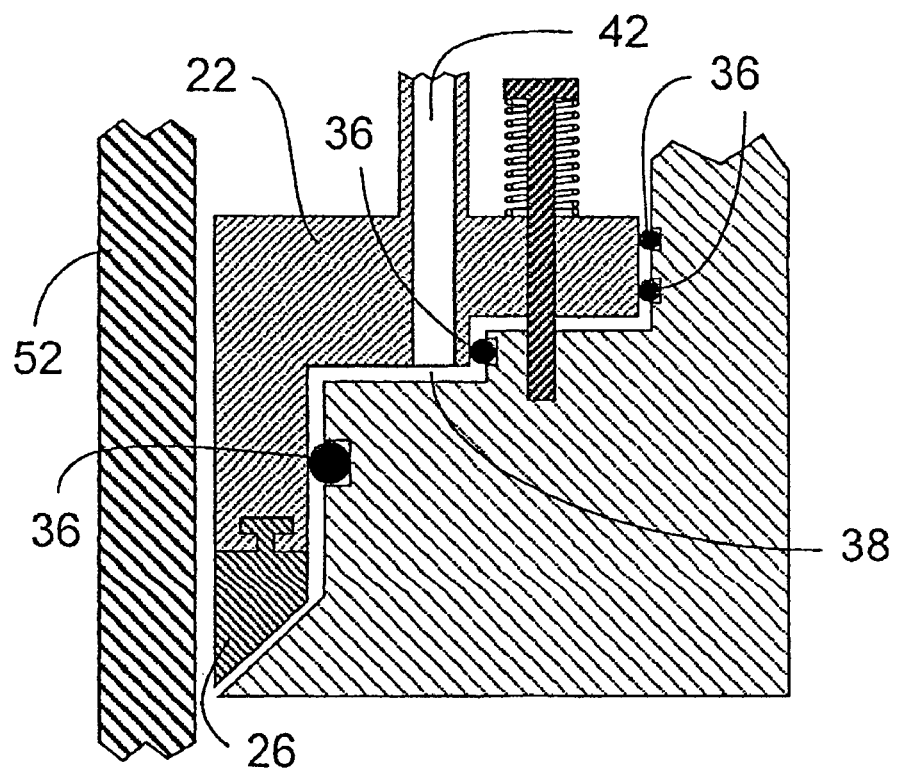
FIG. 3 shows a close up view of the first embodiment of the present invention of FIG. 1 in cross-sectional view.

As shown in FIG. 3 the pressurized energy source 42 has been applied into the space 38 overcoming the bias of the compression means 34 and causing the plate 22 to move away from the flow distributor 2. This causes the seal 26 to move away from the outer edge 18 of the flow distributor 2 releasing the fluid tight seal formed between the two elements 22 and the inner wall of the column 52. In this condition, the flow distributor 2 is now free to move into or out of the column. The pressurizing source enables the operator to adjust the seal from pre-loaded to disengaged with infinite adjustability.

The pin 30 as it is attached to the flow distributor 2 compresses the material and maintains that material under compression. It in turn acts upon flow distributor 2 and the seal plate 22 to create the desired seal. The compression means 34 of FIG. 1 are shown to be disk springs. Other springs, such as helical springs, wound springs and the like may also be used.

Alternatively, one can use a material that can be compressed and kept in that condition so as to apply the desired compression to bias the plate 22 against the flow distributor 2. Such materials include, but are not limited to, rubbers and elastomers such as neoprene, butyl rubber, EPDM, silicone and urethane. They may be solid or formed as a closed cell foam. Alternatively it can be a compressible bag of pressurized gas or liquid. They are typically of a height greater than that when mounted to the pin 30 and typically a compression plate such as a compression washer is mounted above the compression means to allow the movement of the pin to create a compressive force on the compression means and thereby on the plate 22 thereby biasing the plate 22 toward the flow distributor 2. In another alternative arrangement, the pin 30 may incorporate a piston mechanism such as a gas charged or compressed hydraulic fluid piston. Other devices and materials that provide a positive compression may also be used.

Figure 4:
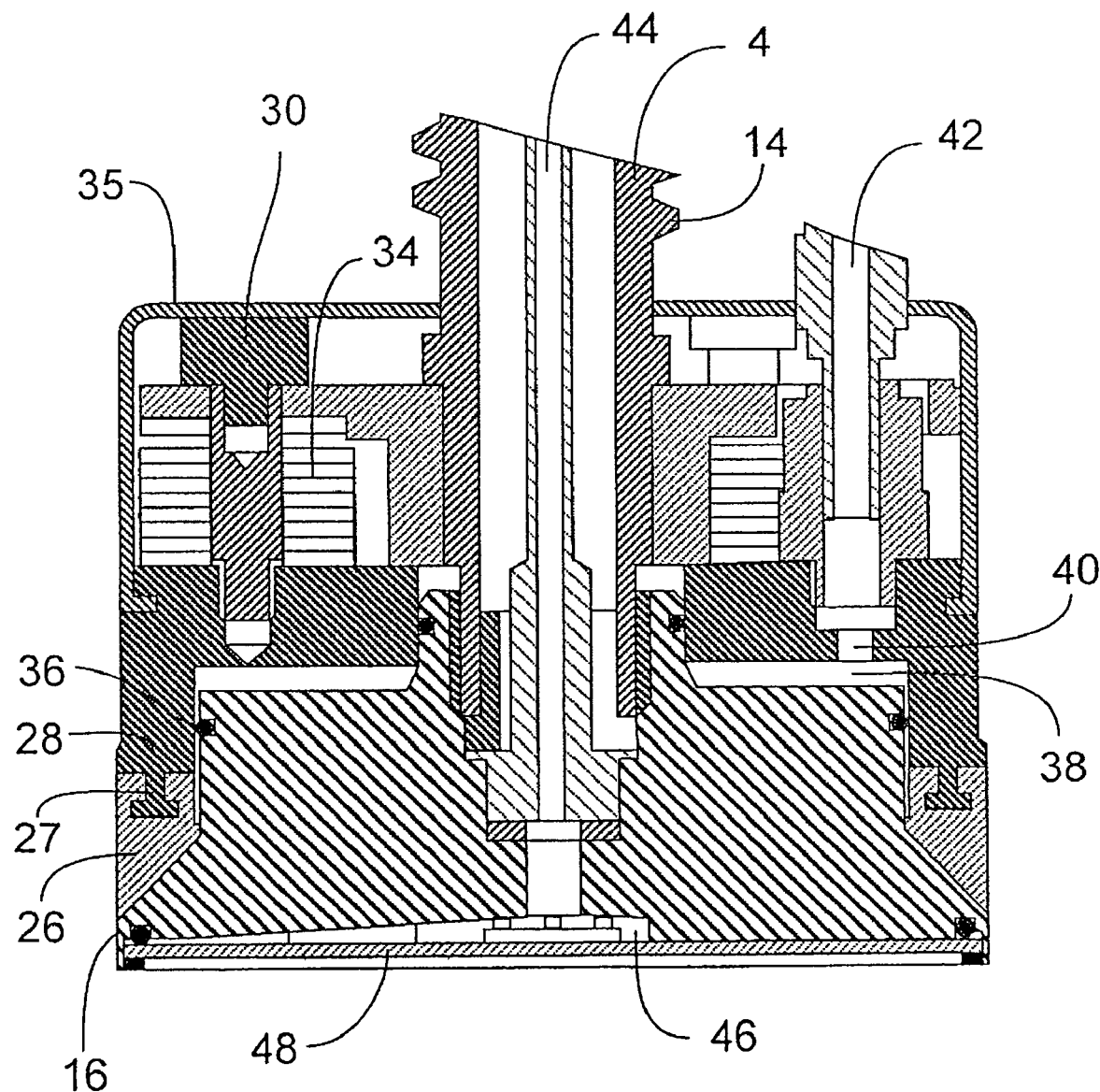
FIG. 4 shows a second embodiment of the present invention in cross-sectional view.

FIG. 4 shows a second embodiment of the present invention that is similar to that of FIG. 1 except the spring load from pins 30 and compression means 34 is not born directly to the flow distributor 2, but instead the load is transferred to the central rod 4, by a retention plate 6.

Figure 5:
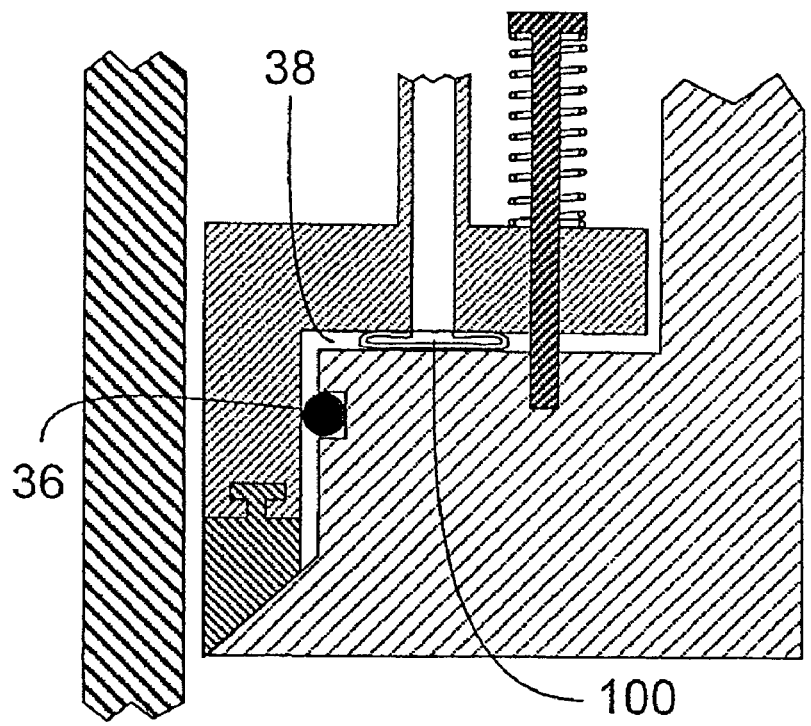
FIG. 5 shows a third embodiment of the present invention in cross-sectional view in the unsealed position.
Figure 6:
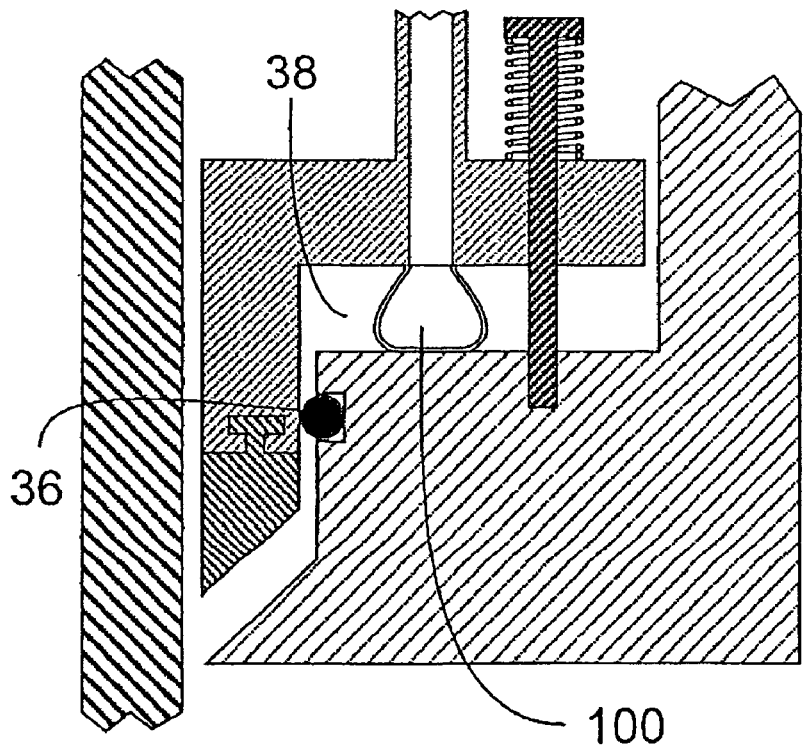
FIG. 6 shows the third embodiment of the present invention in cross-sectional view in the sealed position.

FIGS. 5 and 6 show another embodiment of the present invention. A flexible reservoir 100, in this instance a bladder, is contained within the space 38 formed between the plate 22. No seals 36 are necessary as the pressurized fluid is contained within the bladder. However, for safety reasons, a lower seal 36 is preferably kept to ensure that if a leak occurs, the leak's movement is limited and contamination is avoided.

What we claim:

1. A movable plate for a chromatography column comprising a flow distributor and a seal plate, the seal plate being mounted on top of at least the outer periphery of the flow distributor, the plate being connected to the distributor by one or more pins, the one or more pins having a compression means for normally and positively biasing the plate toward the flow distributor, the compression means for biasing being attached to the pins and acting on an outer surface of the plate, the plate having a seal arranged at its lowermost portion at least on its outer periphery, a space formed between the lower surface of the seal plate and the upper surface of the flow distributor, an opening formed in the seal plate for the selective introduction and removal of a pressurized energy, the energy being selected from the group consisting of compressed air, a compressed gas, water, and a hydraulic fluid, and one or more seals formed between the plate and the flow distributor to contain the pressurized fluid within the space.

2. The device of claim 1 further comprising a bladder contained within the space and attached to the opening for receiving the pressurized energy.

3. The device of claim 1 wherein the compression means is one or more springs.

4. The device of claim 1 wherein the compression means is a material having a stored physical energy potential.

5. The device of claim 1 wherein the compression means is a material having a stored physical energy potential and is selected from the group consisting of compressed elastomers and rubbers.

6. The device of claim 1 wherein the compression means is a material having a stored physical energy potential and is selected from the group consisting of gas sacks and pistons.

7. The device of claim 1 further comprising a bladder contained within the space and attached to the opening for receiving the pressure source.

8. The device of claim 1 wherein the movable plate is a top plate.

9. The device of claim 1 wherein the movable plate is a bottom plate.

10. The device of claim 1 wherein both top plate and the bottom plate are movable.

11. A movable plate for a chromatography column comprising a flow distributor and a seal plate, the seal plate being mounted on top of at least the outer periphery of the flow distributor, the plate being connected to the distributor by one or more pins, the one or more pins having a compression means for normally and positively biasing the plate toward the flow distributor, the compression means for biasing being attached to the pins and acting on an outer surface of the plate, the plate having a seal arranged at its lowermost portion at least on its outer periphery, a space formed between the lower surface of the seal plate and the upper surface of the flow distributor, an opening formed in the seal plate for the selective introduction and removal of a pressurized energy, the energy being selected from the group consisting of compressed air, compressed gases, compressed liquids and a hydraulic fluid, and one or more seals formed between the plate and the flow distributor to contain the pressurized fluid within the space and a bladder contained within the space and attached to the opening for receiving the pressurized energy.

12. The device of claim 11 wherein the movable plate is a bottom plate.

13. The device of claim 11 wherein the movable plate is a top plate.

14. The device of claim 11 wherein both top plate and the bottom plate are movable.

* * * * *

UNITED STATES PATENT AND TRADEMARK OFFICE
CERTIFICATE OF CORRECTION

PATENT NO.        : 7,578,934 B2                                      Page 1 of 1
APPLICATION NO.   : 11/247025
DATED             : August 25, 2009
INVENTOR(S)       : Gill et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 910 days.

Signed and Sealed this

Fourteenth Day of September, 2010

David J. Kappos
*Director of the United States Patent and Trademark Office*